United States Patent
Hwang et al.

(10) Patent No.: US 10,239,928 B2
(45) Date of Patent: Mar. 26, 2019

(54) METHOD OF HIGHLY EXPRESSING TARGET PROTEIN FROM PLANT USING RBCS FUSION PROTEIN AND METHOD OF PREPARING COMPOSITION FOR ORAL ADMINISTRATION OF MEDICAL PROTEIN USING TARGET PROTEIN EXPRESSION PLANT BODY

(71) Applicant: POSTECH ACADEMY-INDUSTRY FOUNDATION, Pohang-si (KR)

(72) Inventors: Inhwan Hwang, Pohang-si (KR); Hyang Ju Kang, Pohang-si (KR); Eun Ju Sohn, Pohang-si (KR); Yong Jik Lee, Pohang-si (KR); Per-Olof Berggren, Pohang-si (KR); Yun Joo Yoo, Pohang-si (KR); Jae Yoon Kim, Pohang-si (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 0 days.

(21) Appl. No.: 15/597,253

(22) Filed: May 17, 2017

(65) Prior Publication Data
US 2017/0335361 A1    Nov. 23, 2017

(30) Foreign Application Priority Data

May 20, 2016 (KR) .................. 10-2016-0062409
Mar. 24, 2017 (KR) .................. 10-2017-0037747

(51) Int. Cl.
| C12N 15/82 | (2006.01) |
| C07K 14/575 | (2006.01) |
| C12N 9/88 | (2006.01) |
| A61K 38/51 | (2006.01) |
| A61K 38/22 | (2006.01) |

(52) U.S. Cl.
CPC ...... *C07K 14/5759* (2013.01); *A61K 38/2264* (2013.01); *A61K 38/51* (2013.01); *C12N 9/88* (2013.01); *C12N 15/8241* (2013.01); *C12Y 401/01039* (2013.01); *C07K 2319/42* (2013.01); *C07K 2319/43* (2013.01)

(58) Field of Classification Search
None
See application file for complete search history.

(56) References Cited

FOREIGN PATENT DOCUMENTS

JP    2002-529079    9/2002

OTHER PUBLICATIONS

Zhang et al, 2002, Plant Cell Physiol., 43:1302-1313.*
Dhingra et al, 2004, PNAS, 101:6315-6320.*
Kay et al, 1987, Science, 236:1299-1302.*
Whitney et al, 2007, Journal of Biological Chemistry, 282:3809-3818.*
Krebbers et al, 1998, Plant Mol. Biol. 11, 745-759.*
NCBI GenBank Accession No. AK319060, "*Arabidopsis thaliana* AT1G67090 mRNA, complete cds, clone: RAFL25-30-K13", GenBank: AK319060.1, Apr. 21, 2009.
M. Muto et al., "Accumulation and processing of a recombinant protein designed as a cleavable fusion to the endogenous Rubisco LSU protein in Chlamydomonas chloroplast", BMC Biotechnology, vol. 9, No. 26, pp. 1-11 Mar. 26, 2009, Research article, BioMed Central.
NCBI GenBank Accession No. X13611, "*Arabidopsis thaliana* ats1A gene for ribulose 1.5-biphoshate carboxylase small subunit (EC 4.1.1.39)", GenBank: X13611.1, Nov. 14, 2006.
H. Ishida et al., "Mobilization of Rubisco and Stroma-Localized Fluorescent Proteins of Chloroplasts to the Vacuole by an ATG Gene-Dependent Autophagic Process", Plant Physiology, Sep. 2008, vol. 148, No. 1, pp. 142-155, American Society of Plant Biologists.
JPO, Office Action of JP 2017-100246 dated Apr. 24, 2018.
KIPO, Office Action of KR 10-2017-0037747 dated Jun. 18, 2018.

* cited by examiner

*Primary Examiner* — Jason Deveau Rosen
(74) *Attorney, Agent, or Firm* — Lex IP Meister, PLLC

(57) ABSTRACT

The present invention provides a plant expressing a target protein, a method of preparing the same and a method of preparing a composition for oral administration of a biopharmaceutical using the same. A target protein expression system using plant cells according to the present invention solves conventional problems in plant cell culture, provides a method of producing a large quantity of target proteins including a biopharmaceutical protein and allowing a target protein to have a resistance to a protease present in a digestive organ, and therefore is very effective to enable commercialization of plant-derived biopharmaceuticals.

13 Claims, 10 Drawing Sheets

Specification includes a Sequence Listing.

RbcS; rubisco small subunit

TP; RbcS transit peptide

F; RbcS full length

WT; wild type

KO; *rbcs 1a* knockout

ID NO: 1.

SEQUENCE LISTING

<160> NUMBER OF SEQ ID NOS: 17

<210> SEQ ID NO 1
<211> LENGTH: 782
<212> TYPE: DNA
<213> ORGANISM: Artificial
<220> FEATURE:
<223> OTHER INFORMATION: rbcS

<400> SEQUENCE: 1

```
atggcttcct ctatgctctc ttccgctact atggttgcct ctccggctca ggccactatg      60
gtcgctcctt tcaacggact taagtcctcc gctgccttcc cagccacccg caaggctaac     120
aacgacatta cttccatcac aagcaacggc ggaagagtta actgcatgca ggtcatttat     180
atttcttctt tcactttttt attattccat atgattttt tcggttcttt cttcgaatct     240
acataaacta atatcattgg aaaaatcgaa aaaataggtg tggcctccga ttggaaagaa     300
gaagtttgag actctctctt accttcctga ccttaccgat tccgaattgg ctaaggaagt     360
tgactacctt atccgcaaca agtggattcc ttgtgttgaa ttcgagttgg aggtaattaa     420
acaaaattta aacatctata taaactagct agatcttagg aaaatttggt ttaatatatt     480
aggatcttga tttatataaa catgttcaaa atgttatctg agtggtttgt aacatgtggt     540
ttgtatagca cggatttgtg taccgtgagc acggtaactc acccggatac tatgatggac     600
ggtactggac aatgtggaag cttcccttgt tcggttgcac cgactccgct caagtgttga     660
aggaagtgga agagtgcaag aaggagtacc ccaatgcctt cattaggatc atcggattcg     720
acaacacccg tcaagtccag tgcatcagtt tcattgccta caagccacca agcttcaccg     780
gt                                                                   782
```

<210> SEQ ID NO 2
<211> LENGTH: 182
<212> TYPE: PRT
<213> ORGANISM: Artificial
<220> FEATURE:
<223> OTHER INFORMATION: rbcS

<400> SEQUENCE: 2

Met Ala Ser Ser Met Leu Ser Ser Ala Thr Met Val Ala Ser Pro Ala

```
            1               5                   10                  15
        Gln Ala Thr Met Val Ala Pro Phe Asn Gly Leu Lys Ser Ser Ala Ala
                        20                  25                  30

Phe Pro Ala Thr Arg Lys Ala Asn Asn Asp Ile Thr Ser Ile Thr Ser
                        35                  40                  45

Asn Gly Gly Arg Val Asn Cys Met Gln Met Gln Val Trp Pro Pro Ile
                    50                  55                  60

Gly Lys Lys Lys Phe Glu Thr Leu Ser Tyr Leu Pro Asp Leu Thr Asp
        65                  70                  75                  80

Ser Glu Leu Ala Lys Glu Val Asp Tyr Leu Ile Arg Asn Lys Trp Ile
                        85                  90                  95

Pro Cys Val Glu Phe Glu Leu Glu His Gly Phe Val Tyr Arg Glu His
                        100                 105                 110

Gly Asn Ser Pro Gly Tyr Tyr Asp Gly Arg Tyr Trp Thr Met Trp Lys
                        115                 120                 125

Leu Pro Leu Phe Gly Cys Thr Asp Ser Ala Gln Val Leu Lys Glu Val
                    130                 135                 140

Glu Glu Cys Lys Lys Glu Tyr Pro Asn Ala Phe Ile Arg Ile Ile Gly
        145                 150                 155                 160

Phe Asp Asn Thr Arg Gln Val Gln Cys Ile Ser Phe Val Ala Tyr Lys
                        165                 170                 175

Pro Pro Ser Phe Thr Gly
                    180

<210> SEQ ID NO 3
<211> LENGTH: 835
<212> TYPE: DNA
<213> ORGANISM: Artificial
<220> FEATURE:
<223> OTHER INFORMATION: 35S promoter

<400> SEQUENCE: 3
agattagcct tttcaatttc agaaagaatg ctaacccaca gatggttaga gaggcttacg      60
cagcaggtct catcaagacg atctacccga gcaataatct ccaggaaatc aaataccttc    120
ccaagaaggt taaagatgca gtcaaaagat tcaggactaa ctgcatcaag aacacagaga    180
aagatatatt tctcaagatc agaagtacta ttccagtatg gacgattcaa ggcttgcttc    240
acaaaccaag gcaagtaata gagattggag tctctaaaaa ggtagttccc actgaatcaa    300
aggccatgga gtcaaagatt caaatagagg acctaacaga actcgccgta aagactggcg    360
aacagttcat acagagtctc ttacgactca atgacaagaa gaaaatcttc gtcaacatgg    420
tggagcacga cacacttgtc tactccaaaa atatcaaaga tacagtctca gaagaccaaa    480
gggcaattga gacttttcaa caagggtaa tatccggaaa cctcctcgga ttccattgcc     540
cagctatctg tcactttatt gtgaagatag tggaaaagga aggtggctcc tacaaatgcc    600
atcattgcga taaggaaag gccatcgttg aagatgcctc tgccgacagt ggtcccaaag     660
atggaccccc acccacgagg agcatcgtgg aaaaagaaga cgttccaacc acgtcttcaa    720
agcaagtgga ttgatgtgat atctccactg acgtaaggga tgacgcacaa tcccactatc    780
cttcgcaaga cccttcctct atataaggaa gttcatttca tttggagaga acacg         835

<210> SEQ ID NO 4
<211> LENGTH: 27
<212> TYPE: DNA
<213> ORGANISM: Artificial
<220> FEATURE:
```

<223> OTHER INFORMATION: HA tag

<400> SEQUENCE: 4
tacccatacg atgttccaga ttacgct                                              27

<210> SEQ ID NO 5
<211> LENGTH: 9
<212> TYPE: PRT
<213> ORGANISM: Artificial
<220> FEATURE:
<223> OTHER INFORMATION: HA tag

<400> SEQUENCE: 5

Tyr Pro Tyr Asp Val Pro Asp Tyr Ala
1               5

<210> SEQ ID NO 6
<211> LENGTH: 29
<212> TYPE: DNA
<213> ORGANISM: Artificial
<220> FEATURE:
<223> OTHER INFORMATION: XbaI-RbcS N-termianl sequence F primer

<400> SEQUENCE: 6
tctagaatgg cttcctctat gctctcttc                                            29

<210> SEQ ID NO 7
<211> LENGTH: 25
<212> TYPE: DNA
<213> ORGANISM: Artificial
<220> FEATURE:
<223> OTHER INFORMATION: BamHI-RbcS C-terminal sequence R primer

<400> SEQUENCE: 7
ggatcctacc ggtgaagctt ggtgg                                                25

<210> SEQ ID NO 8
<211> LENGTH: 33
<212> TYPE: DNA
<213> ORGANISM: Artificial
<220> FEATURE:
<223> OTHER INFORMATION: BamHI-PTH N-termianl sequence F primer

<400> SEQUENCE: 8
ggatccaatc tgtgagtgaa atacagctta tgc                                       33

<210> SEQ ID NO 9
<211> LENGTH: 76
<212> TYPE: DNA
<213> ORGANISM: Artificial
<220> FEATURE:
<223> OTHER INFORMATION: XhoI-stop codon-HA C-terminal sequence R primer

<400> SEQUENCE: 9
ctcgagtcag gaagcgtaat ctggaacatc gtatgggtaa gcccggggct gggatttagc          60
tttagttaat acattc                                                          76

<210> SEQ ID NO 10
<211> LENGTH: 240
<212> TYPE: DNA
<213> ORGANISM: Artificial
<220> FEATURE:
<223> OTHER INFORMATION: rbcS transit peptide

<400> SEQUENCE: 10

```
atggcttcct ctatgctctc ttccgctact atggttgcct ctccggctca ggccactatg    60
gtcgctcctt tcaacggact taagtcctcc gctgccttcc agccacccg caaggctaac    120 aacgacacta cttccatcac aagcaacggc ggaagagtta actgcatgca ggtgtggcct    180
ccgattggaa agaagaagtt tgagactctc tcttaccttc ctgaccttac cgattccggg    240
```

<210> SEQ ID NO 11
<211> LENGTH: 80
<212> TYPE: PRT
<213> ORGANISM: Artificial
<220> FEATURE:
<223> OTHER INFORMATION: rbcS transit peptide

<400> SEQUENCE: 11

```
Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Gly Lys
    50                  55                  60

Lys Lys Phe Glu Thr Leu Ser Tyr Leu Pro Asp Leu Thr Asp Ser Gly
65                  70                  75                  80
```

<210> SEQ ID NO 12
<211> LENGTH: 24
<212> TYPE: DNA
<213> ORGANISM: Artificial
<220> FEATURE:
<223> OTHER INFORMATION: BamHI-leptin N-termianl sequence F primer

<400> SEQUENCE: 12

```
ggatccatgt gctggagacc cctg                                            24
```

<210> SEQ ID NO 13
<211> LENGTH: 70
<212> TYPE: DNA
<213> ORGANISM: Artificial
<220> FEATURE:
<223> OTHER INFORMATION: XhoI-stop codon-HA C-terminal sequence R primer

<400> SEQUENCE: 13

```
ctcgagtcag gaagcgtaat ctggaacatc gtatgggtaa gcccgggggc attcagggct    60
aacatccaac                                                            70
```

<210> SEQ ID NO 14
<211> LENGTH: 117
<212> TYPE: DNA
<213> ORGANISM: Artificial
<220> FEATURE:
<223> OTHER INFORMATION: Exendin-4

<400> SEQUENCE: 14

```
catggtgaag gaacatttac cagtgacttg tcaaaacaga tggaagagga ggcagtgcgg    60
ttatttattg agtggcttaa gaacggagga ccaagtagcg gggcacctcc gccatcg       117
```

<210> SEQ ID NO 15
<211> LENGTH: 39
<212> TYPE: PRT
<213> ORGANISM: Artificial
<220> FEATURE:

```
<223> OTHER INFORMATION: Exendin-4

<400> SEQUENCE: 15

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 16
<211> LENGTH: 36
<212> TYPE: DNA
<213> ORGANISM: Artificial
<220> FEATURE:
<223> OTHER INFORMATION: G15

<400> SEQUENCE: 16
aggtcttcta ctaagcctcc tctttctcct cttggt                              36

<210> SEQ ID NO 17
<211> LENGTH: 12
<212> TYPE: PRT
<213> ORGANISM: Artificial
<220> FEATURE:
<223> OTHER INFORMATION: G15

<400> SEQUENCE: 17

Arg Ser Ser Thr Lys Pro Pro Leu Ser Pro Leu Gly
1               5                   10
```

METHOD OF HIGHLY EXPRESSING TARGET PROTEIN FROM PLANT USING RBCS FUSION PROTEIN AND METHOD OF PREPARING COMPOSITION FOR ORAL ADMINISTRATION OF MEDICAL PROTEIN USING TARGET PROTEIN EXPRESSION PLANT BODY

CROSS-REFERENCE TO RELATED APPLICATION

This application claims priority to and the benefit of Korean Patent Application No. 10-2017-0037747, filed on Mar. 24, 2017, which claims the benefit of Korean Patent Application No. 10-2016-0062409, filed on May 20, 2016, the disclosure of which is incorporated herein by reference in its entirety.

BACKGROUND

1. Field of the Invention

The present invention relates to a plant for expressing a target protein, a method of preparing the same, and a method of producing a target protein using the same, and more particularly, to a technique of fusing a target protein to a ribulose bisphosphate carboxylase/oxygenase small subunit (RbcS), which is a protein present in a chloroplast, and introducing the fusion product to a plant body for mass production, and preparation of a composition for oral administration of a biopharmaceutical using the same.

2. Discussion of Related Art

Biopharmaceuticals are medical substances present in living organisms, and in a broad sense, may be defined as medical products produced on the basis of bioengineering techniques including genetic recombination, cell fusion, cell culture, etc., which are high-end biotechnology. Such biopharmaceuticals are classified into protein drugs, therapeutic antibodies, vaccines, gene therapeutics and cell therapeutics.

These days, most recombinant proteins use higher cells such as animal cells and insect cells as hosts or are produced using microorganisms such as yeasts or bacteria. However, recombinant protein production through animal cell culture needs an expensive medium, has a high probability to contaminate viruses that can be infected to humans, and needs a separate purification process to remove the contaminated viruses due to a probability of the uptake of bovine serum-derived proteins. In addition, bacteria or yeasts facilitate the mass production of recombinant proteins, but never have post-synthetic modification of proteins or are not suitable for producing glycoproteins because they are very different from humans.

For this reason, in recent years, as an alternative production system for recombinant proteins, plant cell culture has attracted much attention. Plant cells are not only infected by animal-derived viruses or pathogenic bacteria but also have no risk of being mixed with animal-derived substances, and therefore the plant cell culture is considered as a safe production system.

However, the plant cell culture exhibits a relatively lower protein expression level and a lower growth rate than different hosts including animal cells. When recombinant proteins are produced in plant bodies to commercialize plant-derived biopharmaceuticals, it is urgent to develop a technique for increasing expression efficiency of an introduced gene.

Meanwhile, protein drugs are most widely used to be administered into a human body in an injectable form and can be the most effective method that can be applied, but they can cause pain in patients. Particularly, in the case of metabolic diseases such as diabetes, it is necessary to administer protein drugs regularly for a long time by injection, and therefore patients with such a disease endure much pain. For this reason, it is urgent to develop a technique for oral administration of protein drugs. Since biopharmaceuticals produced in plant bodies can be orally administered without protein isolation and purification, they can be a dramatic method. However, when protein drugs are orally administered, they can be degraded by pepsin secreted from the stomach and trypsin secreted from the intestines.

SUMMARY OF THE INVENTION

Therefore, the inventors completed the present invention by confirming that an RbcS gene known to be stably present in the form of a protein complex in a chloroplast increases expression of a target protein in plant cells, and a fusion protein between the target protein and RbcS was linked with RbcL to make a macromolecule, thereby highly increasing a resistance to the protein degradation by the existing pepsin described above.

Accordingly, the present invention is directed to providing an RbcS gene fragment and a gene construct for high expression of a target protein.

The present invention is also directed to providing a recombinant expression vector for high expression of a target protein.

The present invention is also directed to providing a transformed plant body that highly expresses target proteins.

The present invention is also directed to providing a method of preparing a transformed plant body that highly expresses target proteins.

The present invention is also directed to providing a method of constructing an expression vector for high expression of target proteins in plant cells to produce a large quantity of target proteins from a plant body by utilizing the vector.

The present invention is also directed to providing a fusion protein in which a target protein is bound with an RbcS peptide fragment.

The present invention is also directed to providing a method of forming a 500 to 800-kD large complex when a target protein is bound with an RbcS peptide fragment to have a resistance to a protease present in a digestive organ.

The present invention is also directed to providing a pharmaceutical composition for oral administration, which includes a fusion protein in which a target protein is bound with an RbcS peptide fragment as an active ingredient.

In one aspect, the present invention provides an RbcS gene fragment, which improves the expression level of a target protein located downstream in plant cells.

In another aspect, the present invention provides a gene construct for high expression of a target protein in which (a) RbcS gene and (b) a gene encoding a target protein are operably linked in order.

According to an exemplary embodiment of the present invention, the RbcS gene may be a polynucleotide sequence represented as SEQ ID NO: 1.

According to another exemplary embodiment of the present invention, the target protein may be, but is not limited to, any one or more selected from the group consisting of an antigen, an antibody, an antibody fragment, a structural protein, a regulatory protein, a transcription factor, a toxin protein, a hormone, a hormone analogue, a cytokine, an enzyme, an enzyme inhibitor, a transport protein, a receptor, a fragment of a receptor, a defense inducer, a storage protein, a movement protein, an exploitive protein and a reporter protein.

According to an exemplary embodiment of the present invention, the gene construct may further include a promoter gene at the 5' end of the RbcS gene, and the promoter may be, but is not limited to, a 35S promoter derived from cauliflower mosaic virus, a 19S RNA promoter derived from cauliflower mosaic virus, a plant actin promoter and a ubiquitin promoter.

According to another exemplary embodiment of the present invention, a protein tag gene may be further included at the 3' end of a gene encoding a target protein, and may be, but is not limited to, any one selected from the group consisting of an Avi tag, a Calmodulin tag, a polyglutamate tag, an E tag, a FLAG tag, a HA tag, a His tag, an Myc tag, a S tag, a SBP tag, an IgG-Fc tag, a CTB tag, a Softag 1 tag, a Softag 3 tag, a Strep tag, a TC tag, a V5 tag, a VSV tag and an Xpress tag.

The present invention also provides a recombinant expression vector including the gene construct.

In still another aspect, the present invention provides a transformed plant body which is transformed with the recombinant expression vector and highly expresses a target protein.

According to an exemplary embodiment of the present invention, the plant may be selected from food crops including rice, wheat, barley, corn, bean, potato, red bean, oat and sorghum; vegetable crops including *Arabidopsis thaliana*, Chinese cabbage, white radish, pepper, strawberry, tomato, watermelon, cucumber, cabbage, oriental melon, pumpkin, spring onion, onion, and carrot; industrial crops including ginseng, tobacco, cotton, sesame, sugarcane, sugar beet, perilla, peanut, and rape; fruit crops including apple tree, pear tree, jujube tree, peach, grape, tangerine, persimmon, plum, apricot, and banana; and flower crops including rose, carnation, chrysanthemum, lily, and tulip, but the present invention is not limited thereto.

In yet another aspect, the present invention provides a method of preparing a transformed plant body for highly expressing a target protein, which includes constructing a recombinant expression vector and introducing the recombinant expression vector into a plant body.

According to an exemplary embodiment of the present invention, the introduction of the recombinant expression vector into a plant body may be selected from, but not limited to, an *Agrobacterium* sp.-mediated method, particle gun bombardment, silicon carbide whiskers, sonication, electroporation and polyethylene glycol (PEG)-mediated transformation.

In yet another aspect, the present invention provides a method of producing a target protein, which includes (a) constructing the recombinant expression vector, (b) preparing a transformed plant body by introducing the recombinant expression vector to a plant, (c) culturing the transformed plant body and (d) isolating and purifying a target protein from the transformed plant body or a culture solution.

According to an exemplary embodiment of the present invention, a transformed plant body may be prepared by introducing the recombinant expression vector into a plant from which an RbcS gene present in a genome is deficient, and thereby a target protein may be effectively produced.

In yet another aspect, the present invention provides a fusion protein which includes a target protein and an RbcS peptide fragment linked to the 5' end of the target protein.

According to an exemplary embodiment of the present invention, the RbcS peptide fragment may be an amino acid sequence represented by SEQ ID NO: 2.

According to an exemplary embodiment of the present invention, the fusion protein may be a 500 to 800-kD large complex. The size of the fusion protein may depend on the size of a target protein linked to the RbcS peptide fragment.

According to an exemplary embodiment of the present invention, the fusion protein has a resistance to a digestive enzyme.

In yet another aspect, the present invention provides a pharmaceutical composition for oral administration, which includes a fusion protein to which an RbcS peptide fragment is linked at the 5' end of a target protein.

In yet another aspect, the present invention provides a pharmaceutical composition for oral administration, which includes a transformed plant body for expressing a fusion protein to which an RbcS peptide fragment is linked at the 5' end of a target protein as an active ingredient.

According to an exemplary embodiment of the present invention, the RbcS peptide fragment may be an amino acid sequence represented by SEQ ID NO: 2.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
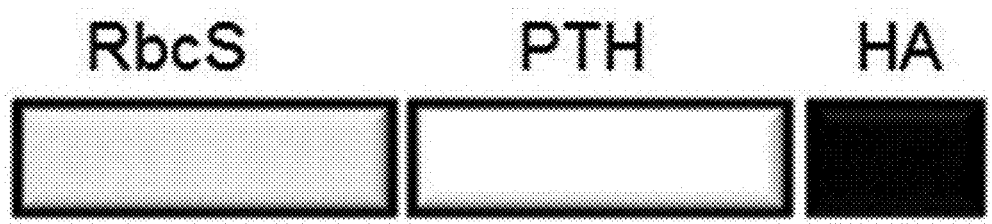
FIG. 1 is a schematic diagram of an RbcS-fusion construct prepared according to an exemplary embodiment of the present invention.

Hereinafter, the present invention will be described in detail.

As described above, to design a method capable of producing a large quantity of target proteins in plant cells, the inventors focused on protein domain fusion capable of stabilizing target proteins in cells, isolated an RbcS gene known to be stably present in the form of a protein complex in the chloroplast of *Arabidopsis thaliana*, and confirmed the fact that when the RbcS gene is fused, expression of target proteins in plant cells is increased (refer to Example 2).

Therefore, the present invention provides an RbcS gene fragment which is characterized by improving the expression level of target proteins located downstream in plant cells.

The RbcS gene may consist of an amino acid sequence of SEQ ID NO: 1. In addition, a variant of the base sequence is included in the scope of the present invention. Specifically, the gene may include a base sequence having 70% or more, preferably 80% or more, more preferably 90% or more, and most preferably 95% or more sequence homology with respect to the base sequence of SEQ ID NO: 1. The "% sequence homology" with respect to a polynucleotide is determined by comparing two optimally-arranged sequences with a comparative region, and a part of the polynucleotide sequence in the comparative region may include addition or deletion (that is, a gap) compared to a reference sequence (without addition or deletion) with respect to the optimal arrangement of two sequences.

In addition, the present invention provides a gene construct for high expression of a target protein, in which (a) an RbcS gene; and (b) a target protein-encoding gene are operably linked in order.

The gene construct of the present invention may further include a promoter gene at the 5' end of the RbcS gene.

The gene construct of the present invention may further include a protein tag gene at the 3' end of a gene encoding a target protein.

In the gene construct of the present invention, (a) a promoter gene; (b) an RbcS gene; (c) a gene encoding a target protein; and (d) a protein tag gene are operably linked in order.

In this case, a promoter may be any one that can express a gene inserted in a plant body without a particular limitation, and is preferably selected from a 35S promoter derived from cauliflower mosaic virus, a 19S RNA promoter derived from cauliflower mosaic virus, a plant actin promoter and a ubiquitin promoter.

The RbcS gene may be a gene encoding RbcS, and most preferably an RbcS gene represented by SEQ ID NO: 1, derived from *Arabidopsis thaliana*.

Here, the target protein is a term referring to a protein to be produced, and is not limited to a specific protein. Specifically, the target protein may be any one or more selected from the group consisting of an antigen, an antibody, an antibody fragment, a structural protein, a regulatory protein, a transcription factor, a toxin protein, a hormone, a hormone analogue, a cytokine, an enzyme, an enzyme inhibitor, a transport protein, a receptor, a fragment of a receptor, a defense inducer, a storage protein, a movement protein, an exploitive protein and a reporter protein.

In one exemplary embodiment of the present invention, as the target protein, parathyroid hormone (PTH) or leptin was used. However, the target protein of the present invention is not limited to leptin or PTH. The present invention may also be used in mass expression of various small peptide-like hormones such as human growth hormone, GLP1, Exendin-4, etc. The expressed protein may be isolated and purified from RbcS by introducing a specific protein degradation site into a fusion part with RbcS.

In addition, the protein tag gene of the present invention may be any distinguishable tag without limitation in order to isolate and purify a protein. Specifically, the protein tag may be any one or more selected from the group consisting of an Avi tag, a Calmodulin tag, a polyglutamate tag, an E tag, a FLAG tag, a HA tag, a His tag, a Myc tag, a S tag, a SBP tag, an IgG-Fc tag, a CTB tag, a Softag 1 tag, a Softag 3 tag, a Strep tag, a TC tag, a V5 tag, a VSV tag and an Xpress tag.

The present invention also provides a recombinant expression vector including the gene construct.

The term "recombinant" is used to refer to cells that replicate heterologous nucleic acids, express the nucleic acids, or express a protein encoded by peptides, heterologous peptides or heterologous nucleic acids. Such recombinant cells may express one of sense and antisense genes or gene fragments, which have not been found in natural cells. In addition, while the recombinant cells may express a gene that is found in natural cells, the gene is modified, and reintroduced to cells by an artificial means.

In the present invention, the RbcS gene sequence may be inserted into a recombinant expression vector. The term "recombinant expression vector" refers to a bacterial plasmid, a phage, a yeast plasmid, a plant cell virus, a mammalian cell virus or a different vector. Generally, any plasmid and vector may be used as long as they can be replicated and stabilized in hosts. The key feature of the expression vector is having a replication origin, a promoter, a marker gene and a translation control element.

An expression vector including the RbcS gene sequence and suitable transcription/translation control signals may be constructed by a method known in the art. The method includes an in vitro recombinant DNA technique, a DNA synthesis technique and an in vivo recombination technique.

The DNA sequence may be effectively linked to a suitable promoter in the expression vector to elicit mRNA synthesis. A vector suitable for expressing the DNA fragment according to the present invention and a gene encoding a target protein in plant cells is a pUC19-based plasmid or Ti plasmid vector.

Exemplary examples of the recombinant vector of the present invention include a part of the vector when the vector is present in suitable hosts such as *Agrobacterium tumefaciens*, and a Ti-plasmid vector which can transfer the so-called T region to plant cells. A different type of Ti-plasmid vector is a protoplast capable of producing a new plant which suitably inserts current plant cells or hybrid DNA into a plant genome to transfer a hybrid DNA sequence. A particularly exemplary form of the Ti-plasmid vector is a so-called binary vector, which has been disclosed in European Patent (EP) No. 0120 516 B1 and U.S. Pat. No. 4,940,838. Another suitable vector that can be used to introduce the DNA according to the present invention into a plant host may be selected from viral vectors derived from a double-stranded plant virus (e.g., CaMV) and a single-stranded virus, for example, a non-competent plant virus vector. The use of such a vector may be particularly advantageous when it is difficult to properly transform a plant host.

Examples of the suitable vectors may include, but are not limited to, a binary vector such as a 326 GFP or pCAMBIA-derived vector, and thus one of ordinary skill in the art can select any vector capable of expressing the DNA fragment according to the present invention and a gene encoding a target protein in plant cells.

More specifically, the recombinant vector is a recombinant expression vector in which a promoter, the DNA fragment according to the present invention to improve an expression level of a target protein, and a gene encoding a target protein are operably linked in order to a conventional vector used in protein expression as a basic backbone.

In addition, the expression vector may include a ribosome-binding site as a translation initiation site and a transcription terminator.

The expression vector may include one or more selectable markers. The marker is a nucleic acid sequence conventionally having a characteristic selected by a conventional chemical method, and includes any gene capable of discriminating transformed cells from untransformed cells. Examples of such genes include, but are not limited to, genes having a resistance to herbicides such as glyphosate and phosphinothricin, genes having a resistance to antibiotics such as kanamycin, G418, bleomycin, hygromycin, and chloramphenicol, and aadA gene.

In the recombinant vector of the present invention, the promoter may be a CaMV 35S, actin, ubiquitin, pEMU, MAS, histone promoter, or Clp promoter, but the present invention is not limited thereto. The "promoter" refers to a DNA region upstream from a structural gene, and a DNA molecule to which an RNA polymerase is bound to initiate transcription. The "plant promoter" is a promoter capable of initiating transcription in plant cells. The "constitutive promoter" is a promoter that is active under most of environmental conditions and developing stage or cell differentiation. Since the selection of transformants can be achieved by various types of tissue in various stages, in the present invention, a constitutive promoter is preferably used. Therefore, a constitutive promoter is not limited in selectability.

In the recombinant vector of the present invention, a conventional terminator may be used, and may be, for example, nopaline synthase (NOS), rice amylase RAmy1 A terminator, phaseolin terminator, Octopine gene terminator of *Agrobacterium tumefaciens*, or *E. coli* rrnB1/B2 terminator, but the present invention is not limited thereto. In terms of the necessity of a terminator, such a region is generally known to increase certainty and efficiency of transcription in plant cells. Therefore, the use of a terminator is very preferable for the scope of the present invention.

Host cells which can stably and sequentially clone and express the vector of the present invention in prokaryotic cells may be any host cells known in the art, and include, for example, *E. coli* JM109, *E. coli* BL21, *E. coli* RR1, *E. coli* LE392, *E. coli* B, *E. coli* X 1776, *E. coli* W3110, *Bacillus* strains such as *Bacillus subtilis* and *Bacillus thuringiensis*, and Enterobacteriaceae strains such as *Salmonella typhimurium, Serratia marcescens* and various *Pseudomonas* sp.

In addition, when the vector of the present invention is transformed in eukaryotic cells, as host cells, yeast cells (*Saccharomyce cerevisiae*), insect cells, human cells (e.g., a Chinese hamster ovary (CHO) cell line, W138, BHK, COS-7, 293, HepG2, 3T3, RIN and MDCK cell lines) or plant cells may be used. The host cells are preferably plant cells, and the plant may be selected from rice, wheat, barley, corn, bean, potato, red bean, oat and sorghum; vegetable crops including *Arabidopsis thaliana*, Chinese cabbage, white radish, pepper, strawberry, tomato, watermelon, cucumber, cabbage, oriental melon, pumpkin, spring onion, onion, and carrot; industrial crops including ginseng, tobacco, cotton, sesame, sugarcane, sugar beet, perilla, peanut, and rape; fruit crops including apple tree, pear tree, jujube tree, peach, grape, tangerine, persimmon, plum, apricot, and banana; and flower crops including rose, carnation, chrysanthemum, lily, and tulip.

A method of delivering the vector of the present invention into host cells may be performed by, when host cells are prokaryotic cells, a $CaCl_2$ method, a Hanahan method (Hanahan, D., *J. Mol. Biol.*, 166:557-580(1983)) or electroporation. In addition, when host cells are eukaryotic cells, the vector may be injected into the host cells by microinjection, calcium phosphate precipitation, electroporation, liposome-mediated transfection, DEAE-dextran treatment, or gene bombardment.

The present invention also provides a transformed plant body which is transformed with the recombinant expression vector and highly expresses a target protein.

According to another exemplary embodiment of the present invention, the plant may be selected from rice, wheat, barley, corn, bean, potato, red bean, oat and sorghum; vegetable crops including *Arabidopsis thaliana*, Chinese cabbage, white radish, pepper, strawberry, tomato, watermelon, cucumber, cabbage, oriental melon, pumpkin, spring onion, onion, and carrot; industrial crops including ginseng, tobacco, cotton, sesame, sugarcane, sugar beet, perilla, peanut, and rape; fruit crops including apple tree, pear tree, jujube tree, peach, grape, tangerine, persimmon, plum, apricot, and banana; and flower crops including rose, carnation, chrysanthemum, lily, and tulip.

The present invention also provides a method of preparing a transformed plant body for highly expressing a target protein, which includes constructing a recombinant expression vector; and introducing the recombinant expression vector into a plant body.

For the introduction of the plant expression vector into plant cells or a plant body, any one method selected from the group consisting of an *Agrobacterium* sp.-mediated method, particle gun bombardment, sonication, electroporation and polyethylene glycol (PEG)-mediated transformation may be used. In one exemplary embodiment of the present invention, for transformation of an *Arabidopsis thaliana* protoplast, PEG-mediated transformation, and for construction of an *Arabidopsis thaliana* transformant, an *Agrobacterium* sp.-mediated method were used.

The present invention also provides a method of producing a large quantity of target proteins using a plant transformed with the recombinant vector of the present invention.

Specifically, the method of producing a target protein of the present invention includes (a) constructing the recombinant expression vector; (b) preparing a transformed plant body by introducing the recombinant expression vector into a plant; (c) culturing the transformed plant body; and (d) isolating and purifying a target protein from the transformed plant body or a culture solution.

In the method of producing a target protein of the present invention, the plant may be a plant from which an RbcS gene present in the genome is deficient.

The method of producing a target protein from the transformed plant cells may obtain a target protein from transformed cells after plant cells are transformed with the recombinant vector according to the present invention and culturing the cells for a suitable time to express the target protein. Here, a method of expressing the target protein is any method known in the art.

In this method, a transformant was constructed with Arabidopsis thaliana, but the present invention is not limited thereto, and the method of the present invention can employ all of protoplasts isolated from dicotyledones or monocotyledones.

The present invention provides a fusion protein including a target protein and an RbcS peptide fragment binding at the 5' end of the target protein.

The fusion protein of the present invention forms a 500 to 800-kD large complex to have a resistance to a protease in a digestive organ.

The present invention also provides a pharmaceutical composition for oral administration, which includes a fusion protein in which an RbcS peptide fragment is bound at the 5' end of a target protein as an active ingredient.

The present invention also provides a pharmaceutical composition for oral administration, which includes a transformed plant body expressing a fusion protein in which an RbcS peptide fragment is bound at the 5' end of a target protein as an active ingredient.

According to an exemplary embodiment of the present invention, the RbcS peptide fragment may be an amino acid sequence represented by SEQ ID NO: 2.

Hereinafter, the present invention will be described in further detail with reference to examples. These examples are merely provided to exemplify the present invention, and it would be obvious to those of ordinary skill in the art as long as the scope of the present invention is not limited by these examples.

Example 1. Construction of Recombinant Expression Vector

The inventors used a gene construct to which [35S promoter]-[RbcS gene]-[target protein gene]-[HA tag] was operably linked as an expression vector (FIG. 1). When a gene encoding a target protein was cloned in an expression vector and then expressed in plant cells, RbcS was expressed in a fused state, transferred to a chloroplast and thus accumulated.

In one example of the present invention, parathyroid hormone (PTH) was used as a target protein, and a method of constructing an expression vector is as follows. PCR was performed with the genomic DNA of Arabidopsis thaliana as a template using a forward primer consisting of a "XbaI-RbcS N-terminal sequence" (SEQ ID NO: 6) and a reverse primer consisting of a "BamHI-RbcS C-terminal sequence" (SEQ ID NO: 7) to amplify an RbcS gene. In addition, PCR was performed with PTH-contained plasmid DNA as a template using a forward primer consisting of a "BamHI-PTH N-terminal sequence" (SEQ ID NO: 8) and a reverse primer consisting of a "XhoI-stop codon-HA C-terminal sequence" (SEQ ID NO: 9) to amplify a HA-tag-fused PTH gene. The amplified PCR products were cleaved with XbaI/BamHI (the first PCR product) and BamHI/XhoI (the second PCR product) and purified, respectively. These two PCR products were cloned between a 35S promoter of cauliflower mosaic virus (SEQ ID NO: 3) and a NOS terminator in a 326 GFP (Arabidopsis Biological Resource Center, Ohio State University, Ohio, USA) plasmid cleaved with XbaI/XhoI, thereby constructing an expression vector RbcS:PTH:HA.

Example 2. Comparison of Protein Expression Effects of RbcS Fusion Vectors

A transformant was prepared by introducing the expression vector prepared in Example 1 into the protoplast separated from a leaf of Arabidopsis thaliana, and amounts of RbcS-fusion proteins expressed from the transformant were compared by western blotting analysis.

Specifically, 30 μg of a cell lysate was mixed with an SDS sample buffer, heated, and then subjected to electrophoresis using a 10% SDS-PAGE gel. A separated protein was transferred to a PVDF membrane, and the reaction was blocked with 5% skim milk. Subsequently, the resulting product was reacted with anti-HA antibodies (1:1,000 dilution), and then reacted with horseradish peroxidase (HRP)-labeled secondary antibodies. Afterward, an ECL solution was treated according to a manufacturer's instruction manual.

Example 3. Analysis of Protein Expression Levels Due to RbcS Fusion in Plant Cells To confirm protein expression levels due to RbcS fusion, a plasmid gene in which an RbcS full length gene (SEQ ID NO: 1) was installed upstream PTH:HA, and as a control, a plasmid gene in which an RbcS transit peptide (SEQ ID NO: 10), instead of the RbcS full length gene, was installed upstream PTH:HA was used. These genes were introduced to protoplasts separated from leaves of Arabidopsis thaliana by PEG-mediated transformation and cultured for 24 hours, the protoplasts were collected, lysed and quantified, followed by western blotting analysis.

Figure 2:
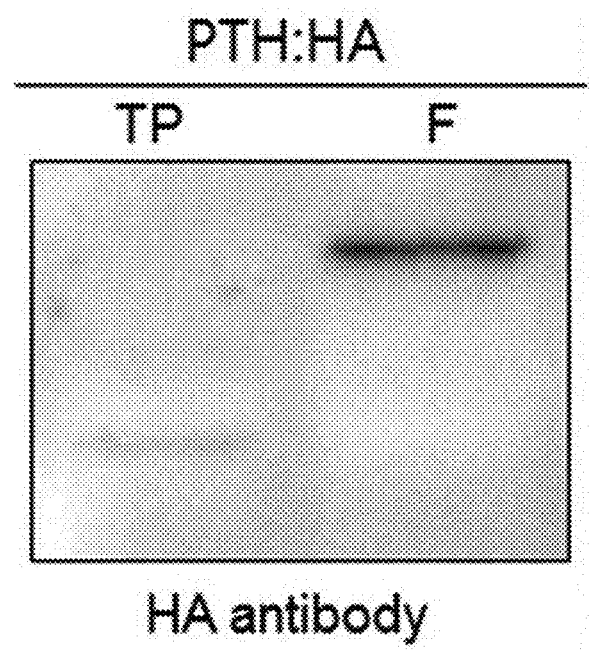
FIG. 2 is an image of western blots confirming that a target protein is highly expressed in plant cells due to RbcS fusion prepared according to an exemplary embodiment of the present invention.

Consequently, referring to FIG. 2, it was shown that the expression of PTH:HA fused with the RbcS full-length gene in the Arabidopsis thaliana protoplast was higher than that of PTH:HA fused with the RbcS transit peptide, which was the control. Accordingly, it can be seen that when the RbcS gene is used as a fusion partner, the expression level of a target protein is improved.

Example 4. Comparative Analysis of Protein Expression Levels Due to RbcS Fusion in Wild-Type Plants and RbcS Gene-Deleted Plants To analyze the expression level of the RbcS-fusion protein in RbcS gene-deficient plants, RbcS gene-deficient mutants of Arabidopsis thaliana were used as host cells.

Specifically, after protoplasts were separated from leaves of wild-type Arabidopsis thaliana and RbcS gene-deficient mutant of Arabidopsis thaliana, respectively, the PTH:HA gene fused with the RbcS full length gene (SEQ ID NO: 1) was introduced to each protoplast by PEG-mediated transformation, and cultured for 24 hours to collect, lyse and quantify protoplasts, followed by western blotting analysis.

Figure 3:
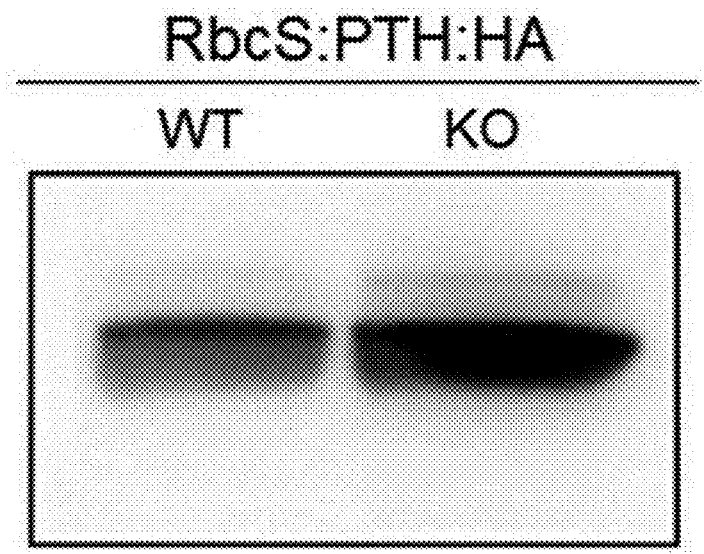
FIG. 3 shows an image of western blots confirming that an RbcS-fusion protein prepared according to an exemplary embodiment of the present invention is more highly expressed in RbcS deletion mutants than normal plants.

As a result, referring to FIG. 3, it was shown that the expression of the PTH:HA fused with the RbcS full length gene is higher in the RbcS gene-deficient mutant of Arabidopsis thaliana than in the wild-type Arabidopsis thaliana. Accordingly, it can be seen that the expression level of a target protein can be effectively improved using a method of expressing the RbcS-fusion protein in the RbcS gene-deficient mutant.

Example 5. Construction of Transformed Plant Body Expressing RbcS Fusion Protein A transformed plant body which is improved in target protein expression due to RbcS fusion was constructed. A plasmid for transforming a plant body was constructed as follows. First, PCR was performed with plasmid DNA containing leptin as a template using a forward primer consisting of "BamHI-leptin N-terminal sequence" (SEQ ID NO: 12 GGATCCATGTGCTGGAGACCCCTG) and a reverse primer consisting of "XhoI-stop codon-HA C-terminal sequence" (SEQ ID NO: 13 ctcgagtcaggaagcgtaatctggaacatcgtatgggtaagcccggggggcattcagggctaacatccaac) to amplify a HA-tag-fused leptin gene. The amplified PCR product was cleaved with BamHI/XhoI, purified and then cloned in RbcS:PTH:HA plasmid DNA cleaved with BamHI/XhoI, thereby constructing RbcS:leptin:HA.

Figure 4:
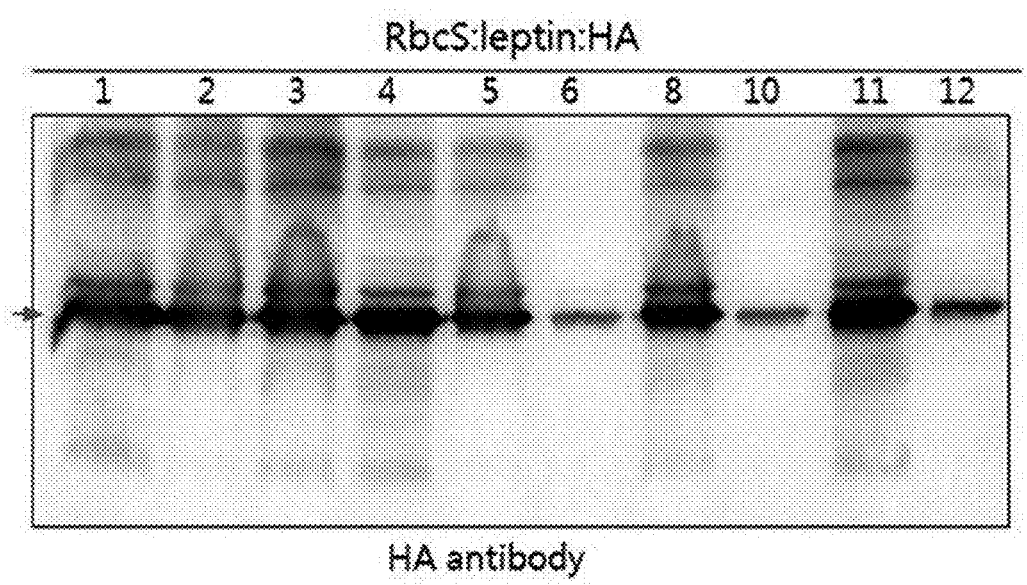
FIG. 4 is an image of western blots confirming that expression of an RbcS-fusion protein in a transformed plant body prepared according to an exemplary embodiment of the present invention.

A recombinant transformation vector was prepared by cloning a 35S promoter-RbcS:leptin:HA:NOS terminator-formed gene construct in a multi-cloning site of a pCAMBIA1300 vector by cleaving an RbcS:leptin:HA-contained region in the prepared recombinant vector using XbaI and EcoRI restriction enzymes. Subsequently, a transformed plant body was manufactured by *Agrobacterium* sp.-mediated transformation using the prepared recombinant transformation vector. Here, the plant body transformed with pCABIA1300, which is a basic vector of the prepared transformation vector was selected by the method of the present invention through a hygromycin resistance test. In addition, the plant body selected by the resistance test was subjected to western blotting to identify a line highly expressing a protein, thereby ensuring first generation transformants (FIG. 4), from second generation transformants, lines clearly exhibiting "dead individuals:live individuals" at a ratio of 1:3 were selected using a hygromycin resistance test, and among these lines, all live individuals from third generation transformants were selected as homo to maintain a line, thereby ensuring a transformed plant body line. Referring to FIG. 4, various bands were observed in transformants 1 to 5, 8 and 11, confirming that a target protein (RbcS:leptin:HA) was highly expressed.

Example 6. Pepsin-Resistant Effect of RbcS-Fused Protein

A transformed plant body of the RbcS-FL:leptin:HA as shown in Example 5 was manufactured and then a resistance against pepsin was investigated in vitro using the plant body.

Figure 5:
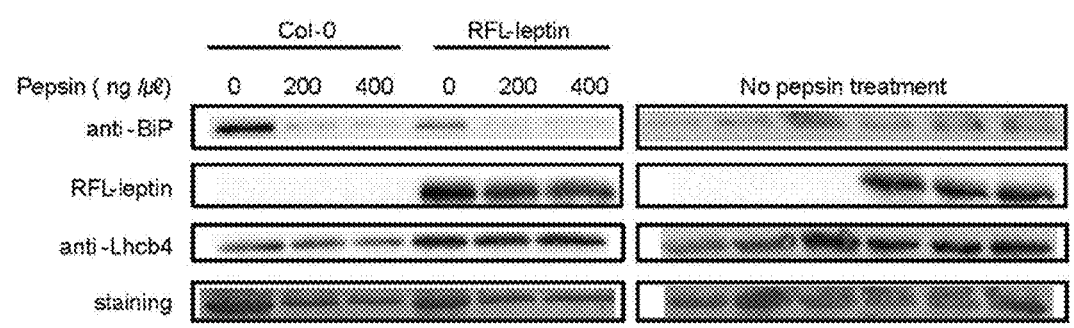
FIG. 5 is a result of an experiment on a pepsin resistance effect per concentration of an RbcS protein-fused target protein (RbcS-FL:leptin:HA) according to an exemplary embodiment of the present invention.

Specifically, after the corresponding transformed plant body was grown for approximately 4 weeks in a green house, leaves were harvested, freeze-dried and then grinded to manufacture a fine powder. A 10 mg aliquot of such a powder-type transformed plant body was mixed with a buffer with pH 2.0, and treated with 0, 200 or 400 ng/μL of pepsin to perform a reaction at 37° C. for 30 minutes. Afterward, the sample was cooled on ice for approximately 10 minutes to reduce the activity of pepsin, and treated with a 1.5 M Tris buffer with pH 8.8 to raise pH and then reduce the activity of pepsin again. Subsequently, cells were disrupted by sonication, mixed with a buffer and boiled for 10 minutes to remove a debris by centrifugation at 14,000 rpm. After then, the sample corresponding to 100 μg was quantified and subjected to SDS-PAGE and then western blotting. As controls to compare a resistance of the fusion protein according to pepsin treatment, an ER protein, which was a chaperone-binding protein (BiP), and a chloroplast protein for forming a complex protein, which was a chlorophyll a-b binding protein (Lhcb4), were used. As a result, referring to FIG. 5, a leptin protein (RFL-leptin) fused with an RbcS full length gene exhibited a higher degradation resistance than Bip in a reaction with a high concentration of pepsin, and exhibited a similar degradation resistance to Lhcb4 for forming another complex.

Figure 6:
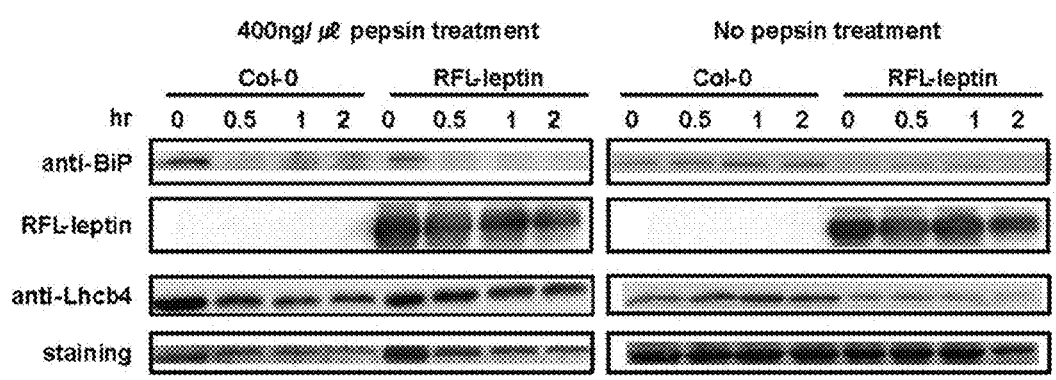
FIG. 6 is a result of an experiment for a pepsin resistance effect per reaction time of an RbcS protein-fused target protein (RbcS-FL:leptin:HA) according to an exemplary embodiment of the present invention.

Here, it was confirmed that the RbcS-fusion protein exhibited a degradation resistance according to pepsin treatment per concentration, and subsequently, the degradation was examined with a reaction time variation of 30 minutes, 1 hour and 2 hours with respect to 400 ng/μL pepsin. Consequently, referring to FIG. 6, although the reaction time was increased, the RbcS-fusion protein still exhibited degradation resistance, unlike other proteins.

Example 7. Confirmation of Stability of RbcS-Leptin in Digestive Tract

To measure the stability of RbcS-FL:leptin:HA protein in a digestive tract, the protein was given to a mouse by a forced diet, and food was obtained from the stomach and the small intestine, followed by western blotting.

Subsequently, leaves of an RbcS-FL:leptin:HA-transformed plant body were freeze-dried under liquid nitrogen, and grinded to manufacture a fine powder. The powder was suspended in PBS, and to exactly control a time in the digestive tract, 80 mg (based on leaf dry weight) of the suspension per individual was directly administered to the stomach of each C57BL/6 mouse (n=5) using zoned. 30 minutes after the administration, food was obtained from the stomach and the small intestine, added to an RIPA lysis buffer, and disrupted by sonication. Cell debris was removed by centrifugation (14,000×g). Following Bradford protein quantification, 20 μg of a protein was loaded in an SDS-PAGE gel to perform western blotting. HA antibodies were used to identify the presence of the RbcS-FL:leptin:HA.

Figure 7:
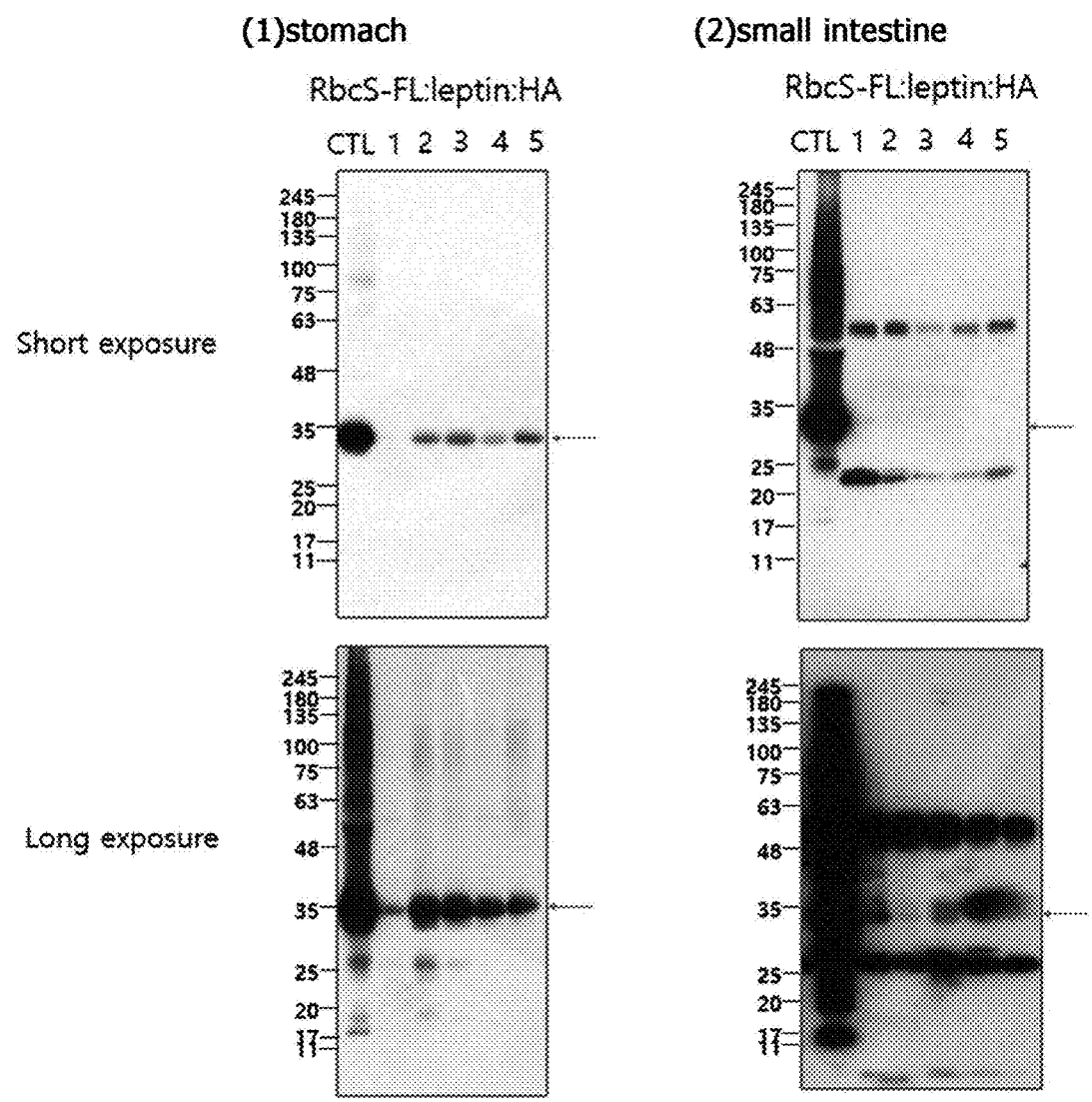
FIG. 7 is a Blue-Native PAGE result confirming that an RbcS protein-fused target protein complex is formed according to an exemplary embodiment of the present invention.

Consequently, referring to FIG. 7, when the food was harvested from the stomach, the original molecular weight of the RbcS-FL:leptin:HA was detected in most individuals. At the same time, compared to the stomach, while it seems that digestion further progressed in the small intestine, the original molecular weight of RbcS-FL:leptin:HA was detected. This showed that when the RbcS-fusion target protein was orally administered, the protein was not degraded by a digestive enzyme but stably present in the digestive tract.

Example 8. Confirmation of Rubisco Complex of RbcS-Fused Protein

To confirm whether the RbcS-FL:leptin:HA prepared in the above-described example still forms a rubisco complex regardless of the fusion of a leptin gene, Blue-Native polyacrylamide gel electrophoresis (PAGE) was performed.

The Blue-Native PAGE analysis is a method of confirming a polymer-form protein, and specifically included the following process. After the transformed plant body was grown in a green house for approximately 4 weeks, leaves were collected therefrom, freeze-dried, and grinded to manufacture a fine powder. 10 mg aliquot of the powder-type transformed plant body was mixed with a Bis-Tris buffer, the cells were disrupted by sonication, quantified and then lysed with a non-ionic detergent, which was n-dodecyl β-D-maltoside. Afterward, following mixing with Coomassie brilliant blue-G250 (CBB-G), electrophoresis was performed in a Blue-Native gel in a 4 to 16% concentration gradient, and then western blotting was performed by the same method as described in the above-described example.

Figure 8:
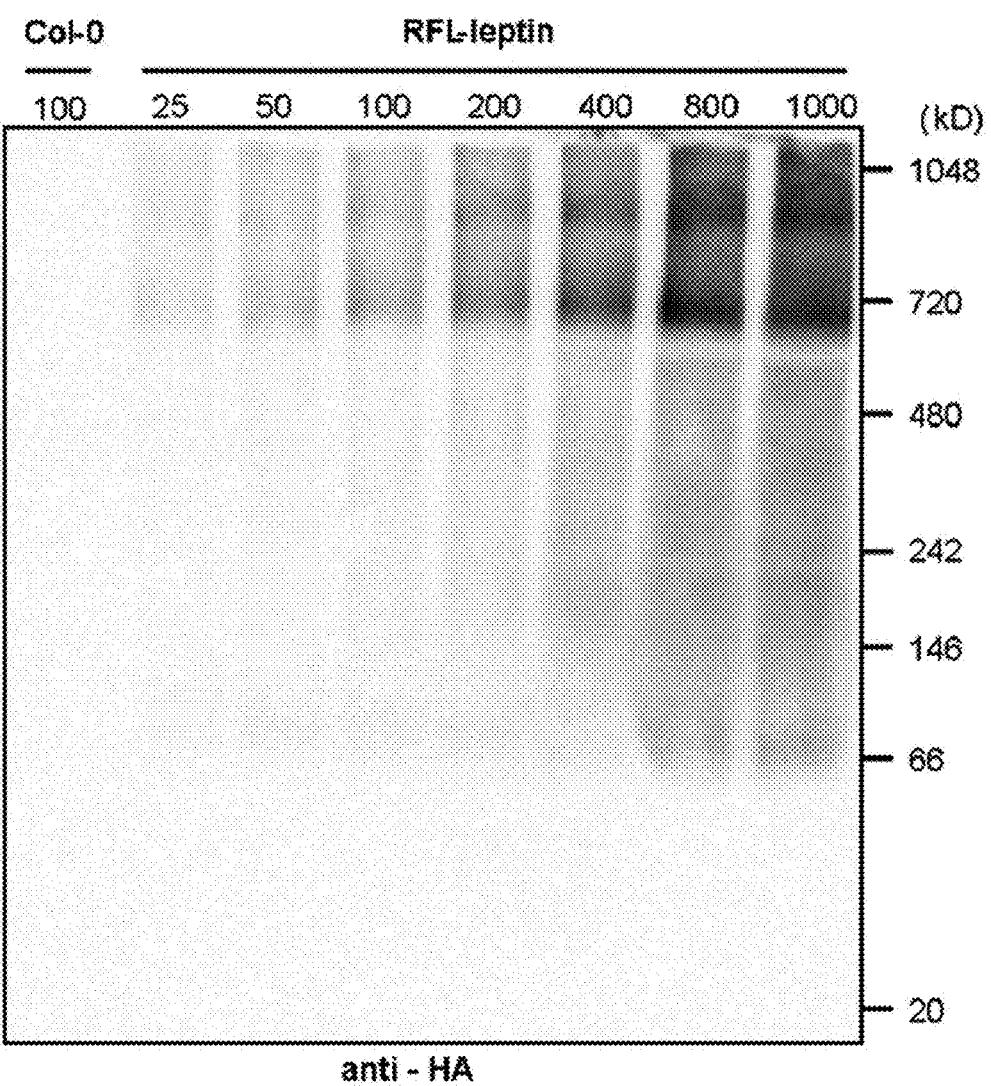
FIG. 8 is a result confirming stability of RbcS-FL:leptin:HA in a digestive tract according to an exemplary embodiment of the present invention.

Consequently, referring to FIG. 8, it was confirmed that the fusion protein forms a rubisco complex.

Example 9. Confirmation of Formation of Rubisco Complex of RbcS-Fused Protein with Different Target Protein As confirmed in Example 8, to further clarify that an RbcS-fusion target protein forms a rubisco complex, an experiment was performed on a different target protein, except leptin.

Figure 9:
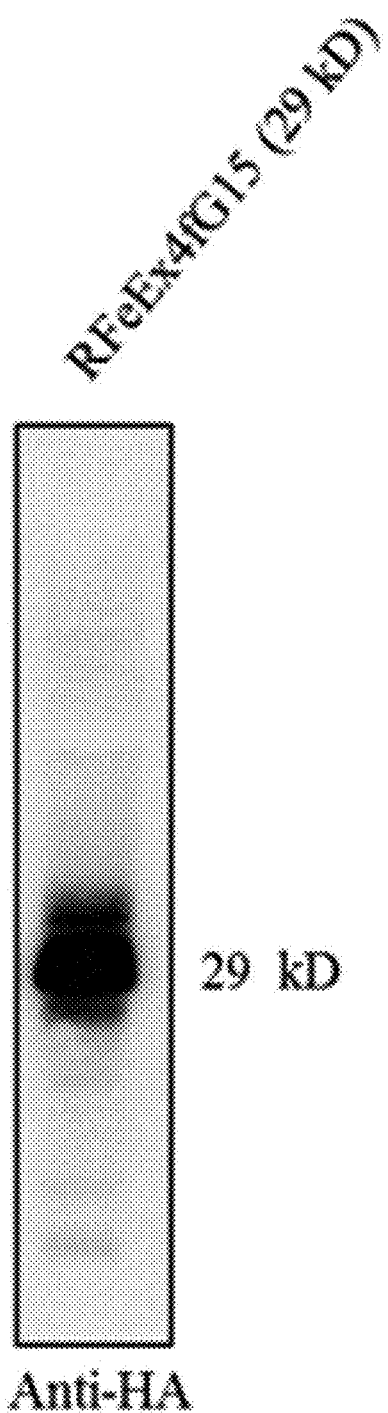
FIG. 9 is a result confirming high expression of a fusion protein RFeEx4fG15 according to an exemplary embodiment of the present invention.

Specifically, the leptin:HA part was removed from the RbcS-leptin:HA recombinant vector, and a DNA fragment in which exendin-4 (SEQ ID NO: 14) and a GM1-binding peptide (G15) (SEQ ID NO: 16) were fused was recombined with the resulting vector (RFeEx4fG15). The prepared recombinant vector was introduced to a protoplast separated from a leaf of *Arabidopsis thaliana* by PEG-mediated transformation, and an amount of the RbcS-fusion protein expressed after 24 hours was detected by western blotting analysis. Consequently, referring to FIG. 9, it was confirmed that a target fusion protein (RFeEx4fG15) was overexpressed in an expected size (29 kD).

Figure 10:
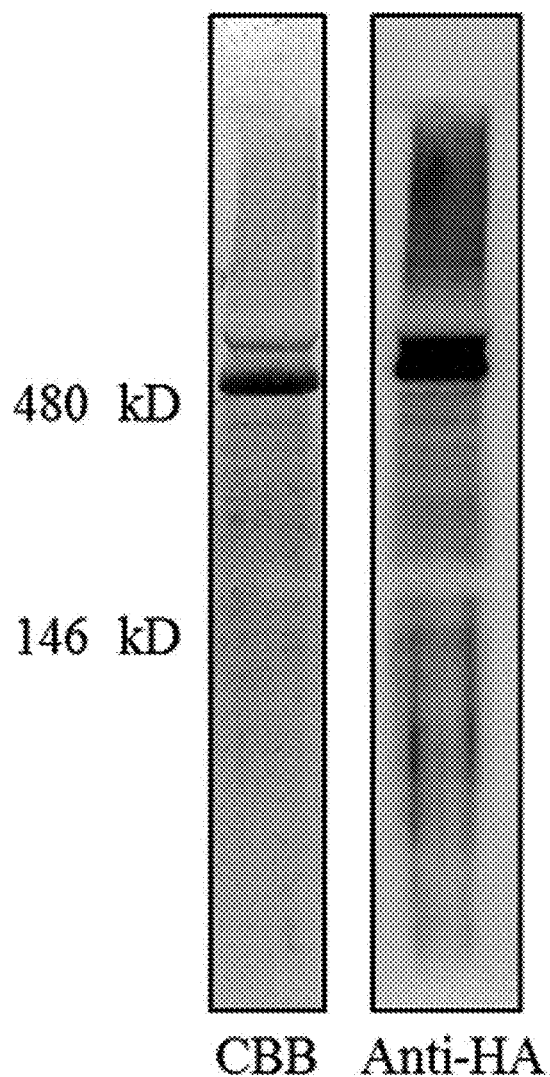
FIG. 10 is a result confirming the formation of a complex between rubisco and a fusion protein RFeEx4fG15 according to an exemplary embodiment of the present invention.

In addition, to confirm whether the target fusion protein (RFeEx4fG15) forms a rubisco complex, a recombinant vector was introduced to a protoplast by the above-described method, and Blue native-PAGE was performed. As a result, referring to FIG. 10, it was confirmed that a fusion protein that had an original size of 29 kD was identified as a larger protein complex than a band observed at approximately 480 kD with Coomassie brilliant blue (CBB) staining, compared to a band (rubisco complex) observed at approximately 480 kD, which indicates that the target fusion protein normally formed the rubisco complex. Therefore, it can be confirmed that, when the RbcS fragment of the present invention was used as a fusion partner regardless of the type of a target protein, the rubisco complex can be stably formed.

Therefore, the present invention provides a plant for expressing a target protein, a method of preparing the same, and a method of producing a target protein using the same. According to the present invention, a target protein can be highly expressed at high efficiency from a plant body and thus can be applied to mass production of an industrial or medical protein using a plant body. Particularly, the plant can be applied to produce a protein drug for oral administration and prepare a pharmaceutical composition for oral administration without isolation and purification of the produced protein.

Above, the present invention has been described with reference to exemplary examples, but it can be understood by those of ordinary skill in the art that the present invention may be changed and modified in various forms without departing from the spirit and scope of the present invention which are described in the accompanying claims.

What is claimed is:

1. A gene construct comprising, (a) an RbcS gene; and (b) a gene encoding a target protein operably linked in order, wherein the RbcS gene is a polynucleotide represented by SEQ ID NO: 1.

2. The gene construct of claim 1, wherein the target protein is any one or more proteins selected from the group consisting of an antigen, an antibody, an antibody fragment, a structural protein, a regulatory protein, a transcription factor, a toxin protein, a hormone, a hormone analogue, a cytokine, an enzyme, an enzyme inhibitor, a transport protein, a receptor, a fragment of a receptor, a defense inducer, a storage protein, a movement protein, and a reporter protein.

3. The gene construct of claim 1, further comprising: a promoter gene at the 5' end of the RbcS gene.

4. The gene construct of claim 3, wherein the promoter is selected from a 35S promoter derived from cauliflower mosaic virus, a 19S RNA promoter derived from cauliflower mosaic virus, a plant actin promoter, and a ubiquitin promoter.

5. The gene construct of claim 1, further comprising: a protein tag gene at the 3' end of the gene encoding the target protein.

6. The gene construct of claim 5, wherein the protein tag is any one selected from the group consisting of an Avi tag, a Calmodulin tag, a polyglutamate tag, an E tag, a FLAG tag, a HA tag, a His tag, an Myc tag, a S tag, a SBP tag, an IgG-Fc tag, a CTB tag, a Softag 1 tag, a Softag 3 tag, a Strep tag, a TC tag, a V5 tag, a VSV tag and an Xpress tag.

7. A recombinant expression vector comprising the gene construct of any one of claims 1, and 2 to 6.

8. A transformed plant body which is transformed with the recombinant expression vector of claim 7.

9. The transformed plant body of claim 8, wherein the plant body is selected from rice, wheat, barley, corn, bean, potato, red bean, oat and sorghum; vegetable crops including *Arabidopsis thaliana*, Chinese cabbage, white radish, pepper, strawberry, tomato, watermelon, cucumber, cabbage, oriental melon, pumpkin, spring onion, onion, and carrot; industrial crops including ginseng, tobacco, cotton, sesame, sugarcane, sugar beet, perilla, peanut, and rape; fruit crops including apple tree, pear tree, jujube tree, peach, grape, tangerine, persimmon, plum, apricot, and banana; and flower crops including rose, carnation, chrysanthemum, lily, and tulip.

10. A method of preparing a transformed plant body which expresses a target protein, comprising:
    constructing the recombinant expression vector of claim 7; and
    introducing the recombinant expression vector into the plant body.

11. The method of claim 10, wherein the introduction of the recombinant expression vector to a plant body is performed by any one or more methods selected from the group consisting of an *Agrobacterium* sp.-mediated method, particle gun bombardment, silicon carbide whiskers, sonication, electroporation and polyethylene glycol (PEG)-mediated transformation.

12. A method of producing a target protein, comprising:
    (a) constructing the recombinant expression vector of claim 7;
    (b) introducing the recombinant expression vector into a plant to prepare a transformed plant body;

(c) culturing the transformed plant body; and
(d) isolating and purifying the target protein from the transformed plant body or a culture solution.

13. The method of claim 12, wherein the plant is a plant from which an RbcS gene present in its genome is deleted.

* * * * *